US010440972B2

(12) United States Patent
Ameye et al.

(10) Patent No.: US 10,440,972 B2
(45) Date of Patent: Oct. 15, 2019

(54) LIQUID MILK FORTIFIER COMPOSITION WITH RELATIVELY HIGH LIPID CONTENT

(71) Applicant: NESTEC S.A., Vevey (CH)

(72) Inventors: Laurent Ameye, Lausanne (CH); Marilisa Hamaoka-Hermann, Vevey (CH); Simona Stan, Rennaz (CH); Sze Tan, Chardonne (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 15/038,619

(22) PCT Filed: Nov. 29, 2013

(86) PCT No.: PCT/EP2013/075058
§ 371 (c)(1),
(2) Date: May 23, 2016

(87) PCT Pub. No.: WO2015/078507
PCT Pub. Date: Jun. 4, 2015

(65) Prior Publication Data
US 2016/0295896 A1 Oct. 13, 2016

(51) Int. Cl.
| | |
|---|---|
| A23C 9/152 | (2006.01) |
| A61K 31/07 | (2006.01) |
| A61K 31/202 | (2006.01) |
| A61K 31/205 | (2006.01) |
| A61K 31/355 | (2006.01) |
| A61K 31/375 | (2006.01) |
| A61K 31/4188 | (2006.01) |
| A61K 31/4415 | (2006.01) |
| A23L 33/00 | (2016.01) |
| A23L 33/115 | (2016.01) |
| A23L 33/12 | (2016.01) |
| A23C 9/158 | (2006.01) |
| A61K 31/047 | (2006.01) |
| A61K 31/122 | (2006.01) |
| A61K 31/14 | (2006.01) |
| A61K 31/185 | (2006.01) |
| A61K 31/197 | (2006.01) |
| A61K 31/201 | (2006.01) |
| A61K 31/455 | (2006.01) |
| A61K 31/51 | (2006.01) |
| A61K 31/519 | (2006.01) |
| A61K 31/525 | (2006.01) |
| A61K 31/59 | (2006.01) |
| A61K 31/685 | (2006.01) |
| A61K 31/70 | (2006.01) |
| A61K 31/714 | (2006.01) |
| A61K 33/00 | (2006.01) |

(Continued)

(52) U.S. Cl.
CPC ............ *A23C 9/1522* (2013.01); *A23C 9/158* (2013.01); *A23C 9/1526* (2013.01); *A23C 9/1528* (2013.01); *A23L 33/115* (2016.08); *A23L 33/12* (2016.08); *A23L 33/15* (2016.08); *A23L 33/16* (2016.08); *A23L 33/40* (2016.08); *A61K 31/047* (2013.01); *A61K 31/07* (2013.01); *A61K 31/122* (2013.01); *A61K 31/14* (2013.01); *A61K 31/185* (2013.01); *A61K 31/197* (2013.01); *A61K 31/201* (2013.01); *A61K 31/202* (2013.01); *A61K 31/205* (2013.01); *A61K 31/355* (2013.01); *A61K 31/375* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/59* (2013.01); *A61K 31/685* (2013.01); *A61K 31/70* (2013.01); *A61K 31/714* (2013.01); *A61K 33/00* (2013.01); *A61K 33/16* (2013.01); *A61K 33/18* (2013.01); *A61K 33/24* (2013.01); *A61K 33/26* (2013.01); *A61K 33/30* (2013.01); *A61K 33/32* (2013.01); *A61K 33/34* (2013.01); *A61K 33/42* (2013.01); *A61K 35/741* (2013.01); *A61K 38/1709* (2013.01); *A23V 2002/00* (2013.01); *A61K 2035/115* (2013.01)

(58) Field of Classification Search
None
See application file for complete search history.

(56) References Cited

U.S. PATENT DOCUMENTS

| | | | |
|---|---|---|---|
| 5,397,589 A * | 3/1995 | Korte | A23C 1/04 426/580 |
| 5,709,888 A | 1/1998 | Gil et al. | |

(Continued)

FOREIGN PATENT DOCUMENTS

| | | |
|---|---|---|
| EP | 2572593 | 3/2013 |
| EP | 2641473 | 9/2013 |

(Continued)

OTHER PUBLICATIONS

Russian Patent Office Communication for related application No. 2016125909/13(040576) dated Feb. 13, 2018, 11 pages.

*Primary Examiner* — Blaine Lankford
(74) *Attorney, Agent, or Firm* — K&L Gates LLP

(57) ABSTRACT

The present invention relates to a liquid milk fortifier composition for administration to infants, which fortifier composition comprises lipids in an amount of above 75% of the caloric content. The fortifier may be administrated to infants either as a supplement to human breast milk or to infant formulas. The present invention also relates to the use of the fortifier composition as well as a kit of parts for use in providing a lipid and/or calorie adapted body weight dependent nutrition to infants.

16 Claims, No Drawings

(51) Int. Cl.
*A61K 33/16* (2006.01)
*A61K 33/18* (2006.01)
*A61K 33/24* (2019.01)
*A61K 33/26* (2006.01)
*A61K 33/30* (2006.01)
*A61K 33/32* (2006.01)
*A61K 33/34* (2006.01)
*A61K 33/42* (2006.01)
*A61K 35/741* (2015.01)
*A61K 38/17* (2006.01)
*A23L 33/15* (2016.01)
*A23L 33/16* (2016.01)
*A61K 35/00* (2006.01)

(56) References Cited

U.S. PATENT DOCUMENTS

| | | | | |
|---|---|---|---|---|
| 6,294,206 B1* | 9/2001 | Barrett-Reis | .......... | A23C 9/206 426/2 |
| 8,545,920 B2* | 10/2013 | Medo | .......... | A23C 9/206 426/580 |
| 9,089,533 B2* | 7/2015 | van der Beek | .......... | A61K 35/20 |
| 9,844,532 B2* | 12/2017 | Lai | .......... | A61K 31/355 |
| 2004/0022922 A1 | 2/2004 | Rutenberg | | |
| 2006/0204632 A1* | 9/2006 | Barrett-Reis | .......... | A23C 9/206 426/580 |
| 2006/0233915 A1* | 10/2006 | Puski | .......... | A23L 2/66 426/72 |
| 2010/0119617 A1 | 5/2010 | O'Connor | | |
| 2013/0059768 A1 | 3/2013 | Hallaraker et al. | | |
| 2016/0022628 A1* | 1/2016 | Lai | .......... | A61K 31/202 514/458 |

FOREIGN PATENT DOCUMENTS

| | | |
|---|---|---|
| RU | 2004133767 | 6/2005 |
| WO | 2010134800 | 11/2010 |
| WO | 2011144340 | 11/2011 |
| WO | 2012078358 | 6/2012 |

* cited by examiner

LIQUID MILK FORTIFIER COMPOSITION WITH RELATIVELY HIGH LIPID CONTENT

CROSS REFERENCE TO RELATED APPLICATIONS

The present application is a National Stage of International Application No. PCT/EP2013/075058, filed on Nov. 29, 2013, the entire contents of which are being incorporated herein by reference.

TECHNICAL FIELD OF THE INVENTION

The present invention relates to a milk fortifier composition, more specifically to a milk fortifier composition comprising a high amount of lipid. In particular the present invention relates to a fortifier composition designed for infant as a supplement to either human breast milk or infant formulas. The invention furthermore relates to the use of said lipid fortifier composition.

BACKGROUND OF THE INVENTION

Infants are born during different stages of development and are as a result thereof therefore born with different sizes and bodyweight. The number of infants born with a low body weight is increasing. For example preterm or premature infants which are infants born before the term of the birth, i.e. before the $37^{th}$ week of gestation, may have a low body weight at birth. Other infants are small for their gestational age, i.e. may for example be born at term, but have a small body weight, such as below 2500 grams. Furthermore, some infants may have a low growth pattern because of medical issues e.g. digestive disorders, diarrhea, disease, trauma, malnutrition or simply because their mother's milk is depleted in fat or has a low fat content. Those infants are in need for catching up growth.

Mother's milk is recommended for all infants. However, in some cases breast feeding is inadequate, unsuccessful or the mother chooses not to breast feed. For infants not being breast fed there are many nutritional formulas which are commercially available and which cover the infant's nutritional requirements, necessary for the infant's growth and development, such as lipids, proteins, carbohydrate, vitamins, minerals.

However, neither the commercially available infant formulas nor human breast milk have a nutritional composition which is optimal for any of the above mentioned infants, since they have higher nutritional needs than infants born under normal conditions and/or growing under normal conditions. In preterm infants, the breast milk manipulation during preparation of feed is also associated with significant fat losses.

The World Health Organization (WHO) has published curves for normal growth of an infant with regard to weight, length and head circumference in relation to the age of the infant. All the infants mentioned above and who require a higher nutritional intake than normal have in common that human milk or infant formulas will not meet their needs for energy and nutrients, such as to obtain a growth rate similar to the WHO recommended growth rate.

The infants who are low in weight or have a slow growth rate for medical reasons therefore need a supplement to the human breast milk or infant formula.

Some nutritional supplements for infant formula or human breast milk are known in the art. However, these supplements focus on supplementation of proteins.

The European patent application EP1871182 relates to a liquid human milk fortifier composition comprising from 15% to 45% by weight protein and having a caloric density of from about 1.25 to 6.0 kcal/ml. The fat content is described to be up to 40% by weight on a dry weight basis.

The PCT patent application, WO 2011/144340 relates to a protein fortifier for use in varying the amount of protein in preterm infant nutrition.

However, the supplements known do not disclose or suggest a fortification composition having a high amount of lipids and lower amount of proteins and carbohydrates to improve the energy and high-quality fats intakes of an infant without supplying unnecessary high amounts of proteins and/or carbohydrates to the infant.

Thus, there is an unmet need in the art for a milk fortifier composition to give to infants to increase the energy and high-quality fats content, such that the growth rate becomes similar to the one of a normal infant as recommended by WHO.

SUMMARY OF THE INVENTION

Thus, an object of the present invention is to provide a liquid milk fortifier composition, which has a high amount of lipid, so that the growth rate of infants fed with the fortifier composition may be increased.

Another object of the invention is to provide a kit of part disclosing said composition.

As mentioned above, infants may be born having different sizes and bodyweights, i.e. infants are not a uniform group with similar nutritional needs. Some infants have a low body weight at birth and therefore need a higher energy content than normal weight infants. Besides, some infants may have a normal weight at birth, but may still need a high energy intake because the infants have an insufficient growth rate, for example because of problems with colic, digestive disorders, diarrhea, or because the mother's milk is nutritionally insufficient. Such infants are in need for catching up growth.

The energy requirement for preterm infants will depend on postconceptional age (higher per kilogram body weight at 24 weeks than at 36 weeks postconceptional age), accumulated nutrient deficits (both pre- and postnatal growth restriction), alterations in body composition, disease, medication and differences in resting energy expenditure. However, common to all infants with a low body weight is that they will need a higher energy intake than infants having an appropriate weight for their age.

However, the volume food, i.e. milk, an infant can ingest per day is restricted. A preterm infant for example is assumed to be able to ingest between 96 and 200 ml fluid per kg per day, preferably 150 to 180 ml per kg per day. An older infant can ingest higher volumes of food (milk) but not unlimited. Thus, if a higher amount of energy intake is desired, it is not possible to increase the volume of the feed to obtain this amount of nutrients, i.e. an infant cannot ingest an increased volume of an infant formula or human milk to meet the requirements. Further, it is not desired to supplement human breast milk or infant formulas with a protein fortifier simply to increase the energy intake of an infant to promote growth, if the infant is not in need of a protein supplement. An excessive intake of proteins is believed to increase the risk of obesity and it requires a high urea excretion in urine such that a high burden is subjected to the kidneys of the infant.

Thus, an object of the present invention is to provide a milk fortifier composition with a high energy content, i.e.

high amount of lipids, which can be supplied to an infant either directly or by fortification (or supplementation) of human milk or of an infant formula with said composition. The composition according to the present invention makes it possible to give infants a supplement of lipids. Hereby, the infant may receive an increased energy intake desired for said infant and on the same time keep the volume administrated to the infant at a level which is tolerated. The growth rate of the infant is hereby improved without administrating unhealthy and unnecessary high amount of other nutrients. Further, the fortifier can bring extra amounts of essential fatty acids and/or supplements of fat-soluble vitamins required for optimal growth. The fortifier composition according to the present invention may also be used for children in general who are in need of catching up growth.

Another advantage of a fortifier composition with a high amount of lipids is that the infant formula or human milk may be fortified with exactly the amount of lipids which is beneficial for the specific infant. For example, an infant can be fed with a feed having an individualized amount of energy which is optimal for the infant, and not be subjected to high amounts of other nutrients which are not required in high amounts for said infant, e.g. carbohydrates. Another example is an infant in need of higher energy content than what is present in the infant's mother's breast milk, but is does not need an increased amount of other nutrients, e.g. proteins, carbohydrates, vitamins, or minerals. With the composition according to present invention, the mother's milk may be supplemented with a lipid rich composition, such that the infant can be fed with a nutritional composition having an optimal energy content and obtain an improved growth rate.

A further advantage of the fortifier composition according to the present invention is to provide an optimal neurodevelopment and lipid-soluble vitamins absorption.

In particular, it is an object of the present invention to provide a milk fortifier composition that solves the problems of the prior art with not being able to provide a human milk or an infant formula with a supplement of lipid without also providing with a high amount of proteins, or other nutrients.

Thus, one aspect of the invention relates to a liquid milk fortifier composition comprising lipid in an amount of above 75% of the caloric content.

Another aspect of the present invention relates to a kit of parts for use in providing a lipid and/or calorie adapted body weight dependent nutrition to infants comprising:

i) a basic nutritional formulation, and ii) said liquid milk fortifier composition.

Yet another aspect of the present invention relates to said composition for use in fortifying human breast milk, an infant formula or a growing-up milk.

Still another aspect of the present invention is to provide a package comprising said composition, wherein the package is a single-dosing device, a multi-dosing device or a pre-filled feeding device.

In general the various aspects of the invention may be combined and coupled in any way possible within the scope of the invention. These and other aspects, features and/or advantages of the invention will be apparent from and elucidated with reference to the embodiments described hereinafter.

The present invention will now be described in more details.

DETAILED DESCRIPTION OF THE INVENTION

Definitions

Prior to discussing the present invention in further details, the following terms and conventions will first be defined.

In the context of the present invention, mentioned percentages are based on the caloric content unless otherwise stated.

Mentioned percentages based pertain to listed ingredients and are based on the active level and, therefore, do not include solvents or by-products that may be included in commercially available materials, unless otherwise specified.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 1 to 9, from 3.6 to 4.6, from 3.5 to 9.9, and so forth. All references to singular characteristics or limitations of the present invention shall include the corresponding plural characteristic or limitation, and vice versa, unless otherwise specified or clearly implied to the contrary by the context in which the reference, is made.

In the context of the present invention, the term "ratio" by weight (weight/weight) refers to the ratio between the weights of the mentioned compounds. For example, a mixture comprising 2 g arachidonic acid (ARA) and 1 g docosahexaenoic acid (DHA) would have a weight ratio which is equal to 2:1 or 2.0 (that is 2 divided with 1). Similarly, a mixture of 1 g ARA and 5 g DHA would have a ratio by weight of ARA and DHA of 1:5, which is equal to 0.20 (that is 1 divided with 5).

The term "and/or" used in the context of the "X and/or Y" should be interpreted as "X", or "Y", or "X and Y".

Unless defined otherwise, all technical and scientific terms used herein have the same meaning as commonly understood by one of ordinary skilled in the art.

The term "infant" will in the context of the present invention mean a child under the age of 2 years, preferable the infant is a child under the age of 12 months, such as under the age of 9 months, particularly under the age of 6 months.

In the context of the present invention the infant may be any term infant or preterm infant. In an embodiment of the invention the infant is selected from the group of preterm infants and term infants.

The term "term infant" refers to infants born at term or 37 weeks or more after the gestation.

The term "preterm infant" refers to infants who are born before the $37^{th}$ week of gestation.

The term "low body weight infants" refers to infants having a body weight below 2.5 kg at birth.

The term "very low body weight infants" refers to infants having a body weight below 1.5 kg at birth.

The term "extreme low body weight infants" refers to infants having a body weight below 1.0 kg at birth.

The term "small for gestational age infant" refers to infants having a birth weight that is more than 2 standard deviations below the mean reference to a birth weight for gestational growth chart or having a birth weight that is less than the 10$^{th}$ percentile of population-based weight data obtained from infants at the same gestational age. The "small for gestational age infants" include infants who are small at birth either from a constitutive or genetic origin or as a consequence of intrauterine growth restriction.

The term "infant formula" as used herein refers to a nutritional composition intended for infants and as defined in *Codex Alimentarius*, (Codex STAN 72-1981) and Infant Specialities (incl. Food for Special Medical Purpose) as defined in *Codex Alimentarius*, (Codex STAN 72-1981). It also refers to a foodstuff intended for particular nutritional use by infants during the first months of life and satisfying by itself the nutritional requirements of this category of person (Article 2(c) of the European Commission Directive 91/321/EEC 2006/141/EC of 22 Dec. 2006 on infant formulae and follow-on formulae). The infant formulas encompass the starter infant formulas and the follow-up or follow-on formulas. Generally a starter formula is for infants from birth as breast-milk substitute, and a follow-up or follow-on formula from the 6th month onwards.

The "growing-up milks" (or GUMs) are given from one year onwards. It is generally a milk-based beverage adapted for the specific nutritional needs of young children. They are nutritional compositions used for feeding children from 12 months to 2-3 years old in combination with other foods.

The composition of the present invention, including the many embodiments described herein, can comprise, consist of, or consist essentially of the essential elements and limitations of the invention described herein, as well as any additional or optional ingredients, components, or limitations described herein or otherwise useful in infant nutritional formula applications.

Liquid:

The term "liquid", as used herein, encompass any water- or oil-based composition, for example a fluid, oil, emulsion or a gel.

Milk fortifier compositions having a liquid form presents some particular benefits in comparison to powder forms. For example liquid formulations might be more convenient if coupled with a packaging that delivers calibrated drops of a certain weight. In this case, it is easier to fortify by a given amount by using a liquid dropper than using a balance and weight the powder. In some countries (e.g. in the United States) the use of liquid products in hospitals is recommended by the authorities (such as the Food Drug Administration) when available, because liquids are considered safer from a microbiological point of view than powders. In addition, liquid formulations are easier to mix with the compositions to be fortified, whereas the powder ones can form lumps.

Fortifier:

By the term "milk fortifier", it is meant any composition used to fortify or supplement either human breast milk, infant formula, growing-up milk or human breast milk fortified with other nutrients.

The term "fortifier" refers to a composition which comprises one or more nutrients having a nutritional benefit for infants, both preterm infants and term infants. The fortifier according to the present invention is rich in lipid and is therefore particularly considered as a lipid fortifier, lipid supplement or the like.

The fortifier composition, according to the present invention can besides from comprising lipid(s) comprise other nutrients, such as e.g. proteins, carbohydrates, vitamins, minerals, probiotics, or prebiotics.

Lipid:

In the context of the present invention, the term "lipid" refers to one or more lipids and may be any free fatty acid or ester of fatty acids that are suitable for being fed to an infant. Lipid includes for example monoglycerides, diglycerides, triglycerides, phospholipids, cholesterol, free fatty acids, derivatives of fatty acids and combinations thereof.

The lipids used to prepare the fortifier can be naturally liquid or solid at room temperature. In some particular embodiments at least a part of the lipids used to prepare the fortifier are naturally liquid at room temperature.

In an aspect of the present invention, the composition comprises lipid in an amount above 75% of the caloric content.

In some embodiments of the invention, lipids are present in an amount of at least 78% of the caloric content, such as at least 80% of the caloric content, in particular at least 85% of the caloric content, such as at least 90% of the caloric content, or at least 95% of the caloric content, or at least 98% of the caloric content.

In some embodiments lipids are present in an amount not exceeding 99% of the caloric content, or in an amount not exceeding 98% of the caloric content, or in an amount not exceeding 95% of the caloric content, or in an amount not exceeding 90% of the caloric content.

In an embodiment of the invention, the lipids are selected from the group of monoglycerides, diglycerides, triglycerides, phospholipids, cholesterol, free fatty acids, derivatives of fatty acids and combinations thereof.

In a particular embodiment of the invention, the lipids are selected from the group of arachidonic acid, docosahexaenoic acid, eicosapentaenoic acid, medium-chain triacylglycerols (MCT), linoleic acid, α-linolenic acid, milk fat, structured lipids phospholipid, and combinations thereof. Structured lipids may be monoglycerides, diglycerides, triglycerides, cholesterol, palmitic acid esterified in the sn-2 position or interesterified palm stearin.

Lipids may be derived from various sources. The lipid source may be any lipid or fat source which is suitable for use in nutritional compositions to be fed to infants, for example some vegetable or animal fats or oils.

In an embodiment of the invention, the lipid is provided from oils or fats.

Preferred lipid sources include coconut oil, soy oil, corn oil, olive oil, safflower oil, medium chain triglycerides (MCT) oil, sunflower oil, palm oil, palm kernel oil, low erucic rapeseed oil (canola oil), marine oil, cottonseed oil, soy lecithin's, palm oil, milk fat, structured lipids, egg-derived oils, fungal oils, algal oils and combinations thereof. Particularly preferred oils are canola oils, soy lecithin, palm olein, and sunflower oil.

Dietary lipids are essential for an infant since they provide the infant with much of his energy needs, such as the essential polyunsaturated fatty acids and lipid soluble vitamins. The amount and composition of dietary lipids affect both the growth pattern and the body composition of the infant.

In an embodiment of the invention, the lipid comprises one or more polyunsaturated fatty acid, preferably long chained polyunsaturated fatty acids.

The polyunsaturated fatty acids, and in particular the long chain ones are important for the cell membrane function and the development of the brain and visual system in infants. Further, the long chain polyunsaturated fatty acids are important in the formation of bioactive eicosanoids. Brain grey matter and the retina are complex neural functions related to energy supply and the composition of dietary fatty acids.

It is assumed that the daily intrauterine fat deposition is 3 g/kg, the fat malabsorption is from 10% to 40% of the intake and that about 15% of fat is lost by unavoidable oxidation and conversion of absorbed triglyceride to deposited triglyceride in tissue. As a result of this, the recommended minimum fat intake is estimated to be 4.8 g/kg body weight per day. Although, some infants with restricted fluid and feed intake may need high fat intake in order to meet the required energy needs. For most preterm infants a reasonable range of fat intake is from 4.8 to 6.6 g/kg per day or from 4.4 to 6.0 g/100 kcal per day.

Further, infants having a low body weight, such as low weight infants, very low weight infants, extreme low weight infants and small weight for gestational age infants, will need a higher energy intake than normal infants with a normal weight. Lipids or fats contribute to a higher energy content than proteins and carbohydrates. There is therefore a need for a composition with a high amount of lipid to feed to such low weight infants to obtain a feed with a high energy content in order to rapidly increase the weight and growth of the infant.

As discussed before, the daily volume a preterm infant can ingest is 200 ml per kg per day. For older infants this volume is higher. Thus, one cannot just increase the volume of intake of a conventional infant formula or human breast milk if higher energy content is needed. Thus, there clearly is a need for a fortifier composition with a high amount of lipid to be given as a supplement to either human breast milk or to conventional infant formulas.

Human breast milk may comprise a different content of lipid and fatty acids profile, and some mother's breast milk has a low content of lipids. Infants born by these mothers will need a supplement of lipids, but not necessarily a supplement of other nutrients such as proteins, carbohydrates, vitamins or minerals. Thus, there is a need for a composition to fortify human breast milk with lipids to overcome these problems with some mothers having fat depleted breast milk.

In a particular embodiment of the invention, the composition comprises arachidonic acid, docosahexaenoic acid, or a combination thereof as the lipid component. The arachidonic acid and docosahexaenoic acid may be alone or in combination with other lipids, such as linoleic acid and/or α-linolenic acid.

The content of arachidonic acid in the composition according to the present invention is preferably at least 0.2% by weight of the total lipid content, such as at least 0.30%, in particular at least 0.38%, even more preferably at least 0.65%, such as 0.70% by weight of total lipid content.

In another particular embodiment the composition comprises arachidonic acid in an amount of up to 2.5% by weight on the total lipid content, such as at in the range of 0.2 to 2.0%, preferably from 0.3 to 1.5%, such as from 0.35 to 1.2%, even more preferably from 0.4 to 0.9% by weight of the total lipid content.

The content of docosahexaenoic acid in the composition according to the present invention is preferably at least 0.18% by weight of the total lipid content, such as at least 0.25%, even more preferably at least 0.45%, such as 0.5% by weight of total lipid content.

In another specific embodiment the composition comprises docosahexaenoic acid in an amount of up to 1.5% by weight on the total lipid content, such as from 0.10% to 1.5%, preferably from 0.14 to 1.0%, such as from 0.16 to 0.80%, even more preferably from 0.18 to 0.65% by weight of the total lipid content.

In an embodiment of the invention, the lipid comprises one or more of phospholipids.

The content of phospholipid in the composition according to the present invention is preferably from 0.5 to 20% by weight of the total lipid content, such as from 0.8 to 15%, even more preferably from 1.0 to 10%, such as from 1.5 to 8% by weight of the total content of lipid.

However in a particular embodiment of the invention, the composition according to the present invention does not comprise any phospholipids.

In still another embodiment of the invention, the composition comprises linoleic acid, α-linolenic acid or a combination thereof as lipid.

In a specific embodiment of the invention, the lipid in the composition comprises linoleic acid in an amount up to 50% by weight of total lipid content, such as from 1.0 to 45%, in particular from 2.0 to 40%, such as from 4.0 to 35%, preferably from 5.0 to 30%, even more preferably from 10.0 to 25%, such as from 8.0 to 23% by weight of the total lipid content.

In another specific embodiment of the invention, the lipid in the composition comprises linoleic acid in an amount of from 5.8 to 32% by weight of total lipid content, preferably from 7.0 to 25%, such as from 10 to 20% by weight of the total lipid content.

In a still specific embodiment of the invention, the composition comprises at least 1.0% linoleic acid by weight of the total lipid content, such as at least 2.5%, preferably at least 5.0%, such as at least 8.0%, even more preferably at least 10.0%, such as at least 12%, in particular at least 15% by weight of the total lipid content.

In another particular embodiment of the invention, the lipid in the composition comprises α-linolenic acid in an amount of at least 0.9% α-linolenic acid by weight of the total lipid content, in particular from 0.9 to 30% by weight of the total lipid content, such as from 1.0 to 25%, preferably from 1.2 to 20%, such as from 1.5 to 18%, even more preferably from 2.5 to 15% by weight of the total lipid content.

In another embodiment of the invention, the composition comprises at least 0.9% α-linolenic acid by weight of the total lipid content, such as at least 1.5%, preferably at least 2.5%, such as at least 3.5%, even more preferably at least 5.0%, such as at least 7%, such as at least 10% by weight of the total lipid content.

Without being bound by any theory, it is believed that α-linolenic acid plays an essential role as a precursor for synthesis of eicopentaenoic acid (EPA) and docosahexaenoic acid (DHA). A reasonable minimum of α-linolenic acid for infants, both term infants and preterm infants, has been estimated to be 55 mg/kg per 35 day, or 50 mg/100 kcal.

The essential polyunsaturated fatty acids, linoleic acid and α-linolenic acid may be added as small amount of oils containing high quantities of preformed long chain polyunsaturated fatty acids such as arachidonic acid and docosahexaenoic acid, e.g. as fish oils or single cell oils. Preferably, the ratio between linoleic acid (C18:2n-6) and α-linolenic acid (C18:3n-3) in the lipid source is in the range of 1:5 to 15:1 (weight/weight), more preferably in the range between 5:1 and 7:1 (weight/weight). The ratio is preferably less than 7:1 (weight/weight).

Further, the ratio between arachidonic acid (C20:4n-6) and docosahexaenoic acid (C22:6n-3) in the lipid source is preferably in the range between 1:5 and 15:1 (weight:weight), preferably in the range from 1:1 to 2:1 (weight/weight).

The lipid may also be eicosapentaenoic acid (20:5n-3). However, the lipid in the composition according to the present invention should not include eicosapentaenoic acid in an amount exceeding 30% of the amount of docosahexaenoic acid present in the composition, since eicosapentaenoic acid competes with arachidonic acid. Besides, the content of eicosapentaenoic acid is low in human breast milk, therefore, it is desired also to have low amounts of eicosapentaenoic acid in a composition according to the present application, and below 30% of the content of the docosahexaenoic acid.

Docosahexaenoic (DHA) and arachidonic acid (ARA) are both known to provide beneficial effects in infants, such as enhancing brain and vision development. DHA and ARA are therefore necessary for infants, both preterm and term infants, but in particular for a preterm infant. Further, DHA and ARA have shown beneficial effects on measures of cognitive development during the first year of life, and on immune phenotypes.

Non-limiting examples of suitable sources of ARA and DHA include marine oil, egg-derived oils, fungal oil, algal oil, and combinations thereof.

In a further embodiment of the invention, the lipid includes medium-chain triacylglycerides (MCT). The content of the medium-chain triglycerides in the composition, if any, should preferably be in an amount of up to 40% by weight of the total content of lipid.

The content of the MCT in the composition should be below 40% by weight of the total content of lipids.

In an embodiment of the invention, the composition comprises at least 20% MCT by weight of the total lipid content, such as at least 25%, preferably at least 30%, such as at least 35%, even more preferably 40% by weight of the total lipid content.

The term "triacylglycerides" may also be referred to as triglycerides.

Vitamins:

The composition according to the present invention may further comprise one or more vitamin. By the term "vitamin" it is understood vitamins which are essential in the daily diet in nutritionally significant amounts.

Examples of vitamins are vitamin A, vitamin B1, vitamin B2, vitamin B6, vitamin B12, vitamin E, vitamin K, vitamin C, vitamin D, folic acid, niacin, biotin, pantothenic acid, riboflavin, thiamine, and choline. The vitamins may be present in the composition alone or as a combination of two or more vitamins.

In a preferred embodiment of the invention, the composition comprises one or more vitamin which is lipid-soluble, for example one or more of vitamin A, vitamin D, vitamin E and vitamin K.

Vitamin D is important for supporting a large number of physiological processes such as neuromuscular function and bone mineralisation. The preferred amount of vitamin D given to an infant in the first months of life is 800-1000 IU per day, i.e. 20-25 µg per day.

Only small amounts of vitamin D are transported to the breast milk. Thus, human breast milk contains low amounts of vitamin D. An infant who is breast fed therefore will need an additional supply of vitamin D. There is therefore a need for a lipid composition to supply energy to an infant which also contributes to the recommended intakes of vitamin D.

An infant is normally fed 5-8 times a day, and the amount of vitamin per serving should therefore not exceed 5.0 µg vitamin D, preferably the amount per serving should be 3-4 µg vitamin D.

The amount of vitamin D in the composition is thus preferably from 75 to 125 µg per 100 g of the total composition, such as from 80 to 120 µg per 100 g of the total composition, even more preferably from 85 to 110 µg per 100 g of the total composition.

In an embodiment of the invention, the composition comprises from 0.5 to 10.0 µg vitamin D per 100 kcal of the composition, such as from 1.0 to 8.0 µg vitamin D per 100 kcal, preferably from 2.0 to 7.0 µg vitamin D per 100 kcal, even more preferably from 3.5 to 5.5 µg vitamin D per kcal of the composition.

Vitamin K is important to help blood to clot. The human breast milk contains low amounts of vitamin K and the infants immature intestinal tract may not produce enough vitamin K to meet the infants own needs.

The amount of vitamin K in the composition according to the present invention is preferably from 50 to 400 µg per 100 g of the total composition, such as from 100 to 300 µg per 100 g of the total composition, preferably 200 µg per 100 g of the total composition.

In an embodiment of the invention, the composition comprises from 1 to 30 µg vitamin K per 100 kcal, such as form 5 to 20 µg vitamin K per 100 kcal, preferably from 7 to 15 µg vitamin K per 100 kcal, even more preferably from 8 to 12 µg vitamin K per 100 kcal.

Vitamin A prevents infections, while vitamin E protects the body from harmful substances and serves as an antioxidant The daily intake of vitamin A in an infant is preferably from 400 to 1000 µg/kg/day.

Thus, in an embodiment of the invention, the composition comprises from 1 to 30 mg vitamin A per 100 g of the total composition, such as from 5 to 20 mg per 100 g of the total composition, preferably from 8 to 15 mg per 100 g of the total composition.

In an embodiment of the invention, the composition comprises from 0.1 to 3.0 mg vitamin A per 100 kcal, such as from 0.2 to 2.0 mg vitamin A per 100 kcal, preferably from 0.3 to 1.2 mg vitamin A per 100 kcal, even more preferably from 0.4 to 0.8 mg vitamin A per 100 kcal.

The daily intake of vitamin E in an infant is preferably 2.2 to 11 mg per day. Thus, in an embodiment of the invention, the composition comprises from 50 to 200 mg vitamin E per 100 g of the total composition, such as from 75 to 150 mg vitamin E per 100 g of the total composition, preferably from 85 to 115 mg vitamin E per 100 g of the total composition.

In an embodiment of the invention, the composition comprises from 1 to 10.0 mg vitamin E per 100 kcal, such as from 2 to 8.0 mg vitamin E per 100 kcal, preferably from 3 to 7 mg vitamin E per 100 kcal, even more preferably from 4 to 6 mg vitamin E per 100 kcal.

Minerals:

In an embodiment of the invention, the composition further comprises one or more mineral.

Examples of minerals are sodium, potassium, chloride, calcium, phosphate, magnesium, iron, zinc, copper, selenium, manganese, fluoride, iodine, chromium, or molybdenum. The minerals are usually added in salt form.

The minerals may be added alone or in combination.

35 In a specific embodiment of the invention, the mineral is calcium.

Protein:

In another embodiment of the invention the composition further comprises protein. The composition may comprise one or more protein.

In an embodiment of the invention, the composition comprises up to 25% protein of the caloric content. In a preferred embodiment of the invention, the composition comprises up to 15% protein, such as up to 10% protein, or up to 8% protein, such as up to 5% protein, even more preferably up to 2% protein based on the caloric content.

In another embodiment of the invention, the composition is free of protein. By "free" is hereby meant that the composition may comprise traceable amounts of protein, such as less than 1% protein.

In the context of the present invention, the term "protein" refers to both proteins derived from a source of protein, to peptides and to free amino acids in general. There can be one or several proteins.

The detailed make-up of the protein source is not believed to be critical. However, it is preferred that the protein source is based on cow's milk proteins such as whey, lactoferrin, casein and mixtures thereof are used, as well as protein sources based on soy.

In an embodiment of the invention, protein, if present, is made of mixtures of casein and whey proteins. The casein to whey ratio is preferably in the range of 30:70 to 70:30, such as 40:60 to 60:40, in particular 45:55 to 40:60, preferably 40:60.

In another embodiment of the invention, the protein, if present, comprises lactoferrin. E.g. the protein is a mixture of whey, casein and lactoferrin, and preferably with the above mentioned ratio between casein and whey.

The protein(s) in the protein source may be intact or hydrolysed or a combination of intact and hydrolysed proteins.

The term "intact" means in the context of the present invention proteins where the molecular structure of the protein(s) is not altered according to conventionally meaning of intact proteins. By the term "intact" is meant the main part of the proteins are intact, i.e. the molecular structure is not altered, for example at least 80% of the proteins are not altered, such as at least 85% of the proteins are not altered, preferably at least 90% of the proteins are not altered, even more preferably at least 95% of the proteins are not altered, such as at least 98% of the proteins are not altered. In a particular embodiment, 100% of the proteins are not altered.

The term "hydrolysed" means in the context of the present invention a protein which has been hydrolysed or broken down into its component peptides or amino acids.

The proteins may either be fully or partially hydrolysed. In an embodiment of the invention at least 70% of the proteins are hydrolysed, preferably at least 80% of the proteins are hydrolysed, such as at least 85% of the proteins are hydrolysed, even more preferably at least 90% of the proteins are hydrolysed, such as at least 95% of the proteins are hydrolysed, particularly at least 98% of the proteins are hydrolysed. In a particular embodiment, 100% of the proteins are hydrolysed.

Hydrolysation of proteins may be achieved by many means, for example by prolonged boiling in a strong acid or a strong base or by using an enzyme such as the pancreatic protease enzyme to stimulate the naturally occurring hydrolytic process.

The protein(s) according to the present invention may also be derived from free amino acids, or a combination of free amino acids and a source of protein, such as whey, lactoferrin and casein.

The whey protein may be a whey protein isolate, acid whey, sweet whey or sweet whey from which the caseinoglycomacropeptide has been removed (modified sweet whey). Preferably, however, the whey protein is modified sweet whey.

Carbohydrates:

The composition of the present invention may also comprise a source of carbohydrates. The composition may comprise one or more carbohydrate.

In an embodiment of the invention, the composition comprises up to 20% carbohydrate of the caloric content. In a particular embodiment of the invention, the composition comprises up to 15% carbohydrate, such as up to 10% carbohydrate, or up to 8% carbohydrate, such as up to 5% carbohydrate, even more preferably up to 2% carbohydrate based on the caloric content.

In another embodiment of the invention, the composition is free of carbohydrate. By "free" it is hereby meant that the composition may comprise traceable amounts of carbohydrates, such as less than 1% carbohydrate.

The preferred source of carbohydrates is lactose although other carbohydrates such as saccharose, glucose, maltodextrin, and/or starch may also be added.

Probiotics:

The composition according to the present invention may optionally comprise other compounds which may have a beneficial effect such as probiotics (like probiotic bacteria), prebiotics, nucleotides, nucleosides and the like in the amounts customarily found in nutritional compositions to be fed to infants.

Strains of *Lactobacillus* are the most common microbes employed as probiotics. However, other probiotic strains than *Lactobacillus* may be used in the present nutritional composition, for example *Bifidobacterium* and certain yeasts and bacilli.

The probiotic microorganisms most commonly used are principally bacteria and yeasts of the following genera: *Lactobacillus* spp., *Streptococcus* spp., *Enterococcus* spp., *Bifidobacterium* spp. and *Saccharomyces* spp.

In some particular embodiments, the probiotic is a probiotic bacterial strain. Probiotic bacteria are bacteria which have a beneficial effect on the intestinal system of humans and other animals.

In some specific embodiments, it is particularly Bifidobacteria and/or Lactobacilli.

A probiotic is a microbial cell preparation or components of microbial cells with a beneficial effect on the health or well-being of the host. Suitable probiotic bacterial strains include *Lactobacillus rhamnosus* ATCC 53103 obtainable from Valio Oy of Finland under the trademark LGG, *Lactobacillus rhamnosus* CGMCC 1.3724, *Lactobacillus paracasei* CNCM I-2116, *Bifidobacterium lactis* CNCM 1.3446 sold by inter alia by the Christian Hansen company of Denmark under the trademark Bb12 and *Bifidobacterium longum* ATCC BAA-999 sold by Morigana Milk Industry Co. Ltd. of japan under the trademark BB536. The amount of probiotic, if present, likewise preferably varies as a function of the age of the infant.

In an embodiment of the invention, the infant formula further includes a probiotic strain such as a probiotic bacterial strain in an amount of from $10^6$ to $10^{11}$ cfu/g of composition (dry weight).

Probiotic bacteria have a beneficial effect on the intestinal flora in a human being, also an infant, therefore it is believed by the inventors of the present invention, without being bound by any theory, that probiotics reduces rates of infant mortality, because the probiotic bacteria compete with the pathogenic bacteria's in the digestive tract.

In an embodiment of the invention, the composition further comprises one or more probiotic.

Prebiotics:

In the context of the present invention, the term "prebiotics" refers to fibers which have a beneficial effect on the intestinal tract of the infant.

Examples of prebiotics may be fructooligosaccharide, galactooligosaccharide, acidic oligosaccharides, human milk oligosaccharide (HMO), or bovine's milk oligosaccharide (BMO) like cow's milk oligosaccharide (CMO) such as "CMOS-GOS". Some examples are N-acetylated oligosaccharides, sialylated oligosaccharides, fucosylated oligosaccharides and any mixtures thereof.

In an embodiment of the invention, the composition further comprises one or more prebiotic.

In another embodiment of the invention, the prebiotic is human milk oligosaccharides.

Human milk comprises contrary to bovine milk about 10-15 g/L of various oligosaccharides. Bovine milk only comprises traces of oligosaccharides. The human milk oligosaccharides are important for digestion since they serve as food for the friendly *Bifidobacterium infantis*.

In a specific embodiment of the invention, the composition comprises a mixture of galactooligosaccharides and fructooligosaccharides, preferably 90% short chain galactooligosaccharides and 10% long-chain fructooligosaccharides such as the product sold under the trademark Raftilose® or 10% inulin such as the product sold under the trademark Raftiline®. This mixture of galactooligosaccharides and fructooligosaccharides has an improved effect, it will increase faecal bifidobacteria counts, reduce stool pH, reduce stool viscosity, and accelerate gastrointestinal transport. Without being bound by any theory, it is also believed that this mixture of galactooligosaccharide and fructooligosaccharide is increasing feeding advancement and reducing the incidence of gastrointestinal complications such as necrotizing enterocolitis, intestinal gas production, intestinal water loss, intestinal flora and possible interaction with other fermentable substances.

A particularly preferred prebiotic is a mixture of galacto-oligosaccharide(s), N-acetylated oligosaccharide(s) and sialylated oligosaccharide(s) in which the N-acetylated oligosaccharide(s) represent 0.5 to 4.0% of the oligosaccharide mixture, the galacto-oligosaccharide(s) represent 92.0 to 98.5% of the oligosaccharide mixture and the sialylated oligosaccharide(s) represent 1.0 to 4.0% of the oligosaccharide mixture. This mixture is hereinafter referred to as "CMOS-GOS". Preferably, a composition for use according to the invention contains from 2.5 to 15.0 wt % CMOS-GOS on a dry matter basis with the proviso that the composition comprises at least 0.02 wt % of an N-acetylated oligosaccharide, at least 2.0 wt % of a galacto-oligosaccharide and at least 0.04 wt % of a sialylated oligosaccharide. WO2006087391 and WO2012160080 provide some examples of production of "CMOS-GOS".

"N-acetylated oligosaccharide" means an oligosaccharide having an N-acetyl residue.

Suitable N-acetylated oligosaccharides include GalNAcα1,3Galβ1,4Glc and Galβ1,6GalNAcα1,3Galβ1,4Glc. The N-acetylated oligosaccharides may be prepared by the action of glucosaminidase and/or galactosaminidase on N-acetyl-glucose and/or N-acetyl galactose. Equally, N-acetyl-galactosyl transferases and/or N-acetyl-glycosyl transferases may be used for this purpose. The N-acetylated oligosaccharides may also be produced by fermentation technology using respective enzymes (recombinant or natural) and/or microbial fermentation. In the latter case the microbes may either express their natural enzymes and substrates or may be engineered to produce respective substrates and enzymes. Single microbial cultures or mixed cultures may be used. N-acetylated oligosaccharide formation can be initiated by acceptor substrates starting from any degree of polymerisation (DP) from DP=1 onwards. Another option is the chemical conversion of keto-hexoses (e.g. fructose) either free or bound to an oligosaccharide (e.g. lactulose) into N-acetylhexosamine or an N-acetylhexosamine containing oligosaccharide as described in Wrodnigg, T. M.; Stutz, A. E. (1999) Angew. Chem. Int. Ed. 38:827-828.

"galacto-oligosaccharide" means an oligosaccharide comprising two or more galactose molecules which has no charge and no N-acetyl residue Suitable galacto-oligosaccharides include Galβ1,6Gal, Galβ1,6Galβ1,4Glc Galβ1,6Galβ1,6Glc, Galβ1,3Galβ1,3Glc, Galβ1,3Galβ1,4Glc, Galβ1,6Galβ1,6Galβ1,4Glc, Galβ1,6Galβ1,3Galβ1,4Glc Galβ1,3Galβ1,6Galβ1,4Glc, Galβ1,3Galβ1,3Galβ1,4Glc, Galβ1,4Galβ1,4Glc and Galβ1,4Galβ1,4Galβ1,4Glc. Synthesised galacto-oligosaccharides such as Galβ1,6Galβ1,4Glc Galβ1,6Galβ1,6Glc, Galβ1,3Galβ1,4Glc, Galβ1,6Galβ1,6Galβ1,4Glc, Galβ1,6Galβ1,3Galβ1,4Glc and Galβ1,3Galβ1,6Galβ1,4Glc, Galβ1,4Galβ1,4Glc and Galβ1,4Galβ1,4Galβ1,4Glc and mixtures thereof are commercially available under the trademarks Vivinal® and Elix'or®. Other suppliers of oligosaccharides are Dextra Laboratories, Sigma-Aldrich Chemie GmbH and Kyowa Hakko Kogyo Co., Ltd. Alternatively, specific glycoslytransferases, such as galactosyltransferases may be used to produce neutral oligosaccharides.

"sialylated oligosaccharide" means an oligosaccharide having a sialic acid residue with associated charge.

Suitable sialylated oligosaccharides include NeuAcα2,3Galβ1,4Glc and NeuAcα2,6Galβ1,4Glc. These sialylated oligosaccharides may be isolated by chromatographic or filtration technology from a natural source such as animal milks. Alternatively, they may also be produced by biotechnology using specific sialyltransferases either by enzyme based fermentation technology (recombinant or natural enzymes) or by microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP) from DP=1 onwards.

Emulsifiers:

If necessary, the composition according to present invention may comprise emulsifiers and/or stabilizers such as lecithin, citric esters of mono- and diglycerides, monoglycerides, diglycerides and the like. This is especially the case if the composition is provided as a combination of oils and an aqueous liquid, e.g. as an emulsion.

Other Ingredients:

The composition may also optionally comprise other substances which may have a beneficial effect such as nucleotides, nucleosides, and the like in the amount customarily found in nutritional compositions to be fed to infants.

Other optional ingredients may be ones normally known for use on food and nutritional products, in particular infant formulas or infant formula fortifiers, provided that such optional materials are compatible with the essential components described herein, are safe and effective for their intended se, and do not otherwise unduly impair product performance.

Non-limiting examples of such optional ingredients include preservatives, anti-oxidants, buffers, colorants, flavours, thickening agents, stabilizers, and other excipients or processing aids.

Preparation:

The composition according to the present invention may be prepared in any suitable manner. For example, a composition may be prepared by blending together the ingredients, such as lipid, protein and carbohydrate in appropriate proportions. If used, emulsifiers may be included in the blend at this stage. The vitamins and minerals may be added at this stage but are usually added later to avoid thermal degradation. Any lipophilic vitamins, such as vitamin A, D, E and K, and emulsifiers may be dissolved into the fat source prior to blending. Water, preferably water which has been subjected to reverse osmosis, may then be mixed in to a liquid mixture.

The liquid mixture may then be thermally treated to reduce bacterial loads. For example the liquid mixture may be rapidly heated to a temperature on the range of about 80° C. to about 110° C. for about 5 seconds to about 5 minutes. This may be carried out by steam injection or by heat exchanger, for example a plate heat exchanger.

The liquid mixture may then be cooled to about 60° C. to about 85° C., for example by flash cooling. The liquid mixture may then be homogenised, for example in two stages at about 7 MPa to about 40 MPa in the first stage and about 2 MPa to about 14 MPa in the second stage. The homogenised mixture may then be further cooled and any heat sensitive components, such as vitamins and minerals may be added. The pH of the homogenised mixture is conveniently standardised at this point.

The homogenized liquid mixture is then filled into suitable containers, preferably aseptically. However, the liquid composition may also be reported in the container. Suitable apparatus for carrying out filling of this nature is commercially available.

An aspect of the present invention relates to the composition for use in fortifying human breast milk, an infant formula or a growing-up milk, in particular for use in fortifying a human breast milk which is low in fat, i.e. lower than usual or lower in comparison to the nutritional needs of the infant.

In another aspect of the invention, the composition is used in administration to an infant or child for increasing the growth of said infant or child and/or the energy intake of an infant or child.

The present invention also refers to use of the composition to increase the growth of an infant or child and/or the energy intake of an infant or child.

The present invention also refers to a method for increasing the growth of an infant or child and/or the energy intake of an infant or child, comprising administering the composition of the invention to said infant or child.

A further aspect of the invention relates to the use of the composition to fortify an infant formula, human breast milk or a growing-up milk.

The present invention also refers to a method for fortifying an infant formula, human breast milk or a growing-up milk, comprising the addition of the composition according to the invention.

Still another aspect of the invention relates to a kit of parts for use in providing a lipid and/or calorie adapted body weight dependent nutrition to infants [both term and preterm] comprising:

i) a basic nutritional formulation
ii) the liquid milk fortifier according to the present invention.

The present invention also refers to the use of a kit of parts for providing a lipid and/or calorie adapted body weight dependent nutrition to infants, said kit-of-part comprising:

i) a basic nutritional formulation
ii) the liquid milk fortifier composition according to the invention.

The present invention also refers to a method for providing a lipid and/or calorie adapted body weight dependent nutrition to infants, said method comprising administering to said infants a kit-of-part comprising:

i) a basic nutritional formulation
ii) the liquid milk fortifier composition according to the invention.

Examples of a basic nutritional formulation may be an infant formula (including the follow-on formula or toddler formula), human breast milk, fortified human breast milk, growing-up milk.

In an embodiment of the invention, the kit is used for preterm infants and term infants.

The infant may in a particular embodiment of the invention be selected from the group of low body weight infants, very low body weight infants, extreme low body weight infants, small for gestational age infants or infants or children in need for catching up growth.

A still further aspect of the invention relates to a package comprising the composition according to the invention, wherein the package is a single-dosing device, a multi-dosing device or a pre-filled feeding device.

In a specific embodiment of the invention, the package is a syringe, pouch, stick pack, or bottles.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Example 1

An example of a composition according to the present invention is given below:

| Nutrient | Per 100 kcal |
| --- | --- |
| Energy (kcal) | 100 |
| Lipid (g) | 9.76 |
| DHA (mg) | 37.26 |
| Linoleic acid (mg) | 1124.76 |
| α-linolenic acid (mg) | 107.1 |
| ARA (mg) | 47.68 |
| ARA/DHA ratio | 1.28 |
| Linoleic/α-linolenic ratio | 10.5 |
| EPA (mg) | 4.06 |
| EPA/DHA ratio | 0.11 |
| MCT (g) | 1.4 |
| Protein (g) | 0.7 |
| Carbohydrate (g) | 2.3 |
| Minerals and electrolytes | |
| Na (mg) | 71.25 |
| K (mg) | 113.62 |
| Cl (mg) | 100.12 |

-continued

| Nutrient | Per 100 kcal |
|---|---|
| Ca (mg) | 116.41 |
| P (mg) | 69.27 |
| Mg (mg) | 8.50 |
| Mn (μg) | 7.40 |
| Fe (mg) | 2.11 |
| Cu (mg) | 0.10 |
| Zn (mg) | 1.48 |
| I (μg) | 33.76 |
| Se (μg) | 6.75 |
| F (μg) | 1.40 |
| Cr (μg) | 0.88 |
| Mo (μg) | 0.93 |
| Vitamins and trace elements | |
| Vitamin A (μg) | 518.04 |
| Vitamin D (μg) | 4.61 |
| Vitamin E (mg) | 4.3 |
| Vitamin K (μg) | 8.3 |
| Vitamin C (mg) | 24.4 |
| Vitamin B1 (mg) | 0.159 |
| Vitamin B2 (mg) | 0.227 |
| Niacin (mg) | 1.99 |
| Vitamin B6 (mg) | 0.16 |
| Folic acid (μg) | 50.17 |
| Vitamin B12 (μg) | 0.26 |
| Pantothenic acid (mg) | 1.08 |
| Biotin (μg) | 4.70 |
| Cholin (mg) | 10.01 |
| Inositol (mg) | 5.59 |
| Taurine (mg) | 6.98 |
| Carnitine (mg) | 4.89 |

The composition according to the present invention may be fed to an infant as a nutritional supplement to increase the energy. The composition may be added to human breast milk, to an infant formula, a fortified infant formula or to any nutritional composition suitable to be fed to an infant from birth.

The composition is particularly suitable for being fed to an infant as a supplement from the birth of the infant and up to the age of 24 months.

The composition according to the present invention may be formulated with many variations without departing from the scope of the invention as defined in the claims.

All the embodiments as described in the above description shall be interpreted as illustrative and not in a limiting sense.

The invention claimed is:

1. A method for fortifying a product selected from the group consisting of human breast milk, an infant formula and a growing-up milk, the method comprising adding a liquid milk fortifier composition to the product, the liquid milk fortifier composition comprising lipid in an amount of above 75% of the caloric content of the liquid milk fortifier composition, the lipid comprises medium-chain triglycerides in an amount of 20% to 40% by weight of a total content of the lipid and further comprises alpha-linolenic acid in an amount of 0.9% to 30% by weight of the total content of the lipid.

2. A method for increasing the growth and/or the energy intake of an infant or a child, the method comprising administering to the infant or child a composition comprising a liquid milk fortifier composition comprising lipid in an amount of above 75% of the caloric content of the liquid milk fortifier composition, the lipid comprises medium-chain triglycerides in an amount of 20% to 40% by weight of a total content of the lipid and further comprises alpha-linolenic acid in an amount of 0.9% to 30% by weight of the total content of the lipid.

3. The method according to claim 1, wherein the lipid further comprises a component selected from the group consisting of monoglycerides, diglycerides, phospholipids, cholesterol, free fatty acids, derivatives of fatty acids, and combination s thereof.

4. The method according to claim 1, wherein the lipid comprises phospholipid.

5. The method according to claim 1, wherein the lipid further comprises a component selected from the group consisting of arachidonic acid, docosahexaenoic acid, eicosapentaenoic acid, linoleic acid, phospholipid, milk fat, structured lipids, and combinations thereof.

6. The method according to claim 1, wherein the liquid milk fortifier composition further comprises one or more vitamins.

7. The method according to claim 6, wherein the one or more vitamins are lipid-soluble.

8. The method according to claim 1, wherein the liquid milk fortifier composition further comprises one or more minerals.

9. The method according to claim 1, wherein the liquid milk fortifier composition further comprises protein.

10. The method according to claim 1, wherein the liquid milk fortifier composition further comprises carbohydrates.

11. The method according to claim 1, wherein the liquid milk fortifier composition further comprises probiotics.

12. The method according to claim 1, wherein the liquid milk fortifier composition further comprises prebiotics.

13. The method according to claim 1, wherein the lipid is provided by one or more oils or fats.

14. The method according to claim 13, wherein the one or more oils or fats are selected from the group consisting of coconut oil, soy oil, corn Oil, olive oil, safflower oil, medium chain triglyceride oil, sunflower oil, palm oil, palm kernel oil, canola oil, marine oil, cottonseed oil, milk fat, egg-derived oils, fungal oils, algal oils, structured lipids, and combinations thereof.

15. The method according to claim 1, wherein the lipid further comprises arachidonic acid that is 0.2 to 2 wt. % of the total content of the lipid and docosahexaenoic acid that is 0.1 to 1.5 wt. % of the total content of the lipid.

16. The method according to claim 1, wherein the lipid further comprises phospholipid in an amount of 0.5% to 20% by weight of the total content of the lipid.

* * * * *